United States Patent
Park et al.

(10) Patent No.: US 9,431,671 B2
(45) Date of Patent: Aug. 30, 2016

(54) MICROBIAL FUEL CELL COMPRISING A MICROPROBE ARRAY

(75) Inventors: Jae-Hyoung Park, Gyeonggi-do (KR); Seung-Ki Lee, Seoul (KR)

(73) Assignee: Industry-Academic Cooperation Foundation, Dankook University, Gyeonggi-do (KR)

(*) Notice: Subject to any disclaimer, the term of this patent is extended or adjusted under 35 U.S.C. 154(b) by 365 days.

(21) Appl. No.: 14/007,566

(22) PCT Filed: Mar. 22, 2012

(86) PCT No.: PCT/KR2012/002084
§ 371 (c)(1),
(2), (4) Date: Nov. 20, 2013

(87) PCT Pub. No.: WO2012/134104
PCT Pub. Date: Oct. 4, 2012

(65) Prior Publication Data
US 2014/0087213 A1   Mar. 27, 2014

(30) Foreign Application Priority Data
Mar. 25, 2011   (KR) ........................ 10-2011-0026694

(51) Int. Cl.
*H01M 8/02* (2016.01)
*H01M 8/16* (2006.01)
*C12Q 1/02* (2006.01)

(52) U.S. Cl.
CPC .................. *H01M 8/16* (2013.01); *C12Q 1/02* (2013.01); *H01M 8/0204* (2013.01); *H01M 8/0247* (2013.01); *Y02E 60/527* (2013.01)

(58) Field of Classification Search
CPC ............... H01M 8/16; H01M 8/0232; H01M 8/04097; H01M 8/241; H01M 8/0204; H01M 8/0247; H01M 8/0234
See application file for complete search history.

(56) References Cited

U.S. PATENT DOCUMENTS

| | | | |
|---|---|---|---|
| 2005/0150767 A1 | 7/2005 | Su et al. | |
| 2007/0048577 A1* | 3/2007 | Ringeisen | H01M 8/0232 429/401 |
| 2011/0014549 A9* | 1/2011 | Minteer | C12N 11/04 429/523 |

FOREIGN PATENT DOCUMENTS

| | | |
|---|---|---|
| JP | 2009-140781 A | 6/2009 |
| KR | 10-1998-0048923 A | 9/1998 |
| KR | 10-2002-0086625 A | 11/2002 |
| KR | 10-2008-0080105 A | 9/2008 |

OTHER PUBLICATIONS

"Microfabricated Microbial Fuel Cell Arrays Reveal Electrochemically Active Microbes", Hou et al., PLoS ONE, vol. 4, Issue 8, p. 1-8, Aug. 2009.*

(Continued)

*Primary Examiner* — Kenneth Douyette
(74) *Attorney, Agent, or Firm* — Osha Liang LLP

(57) ABSTRACT

Provided is a microbial fuel cell (MFC). The MFC includes a microfluidic element having an inlet portion and an outlet portion for intake and discharge of a culture fluid containing cells and a microchannel portion for capturing the cells and interconnecting the inlet portion and the outlet portion, a microprobe-array element having microprobes as anodes for extracting electrons produced during a metabolic process of the cells, and delivering the extracted electrons to an external circuit outside the cells, and a cathode for delivering the electrons used in the external circuit to an electron acceptor outside the cells. The microprobes penetrate the microfluidic element and are inserted into a plurality of single cells captured by the microchannel portion when the microfluidic element and the microprobe-array element are coupled together. The microprobes are separated from the single cells when the microfluidic element and the microprobe-array element are separated from each other.

8 Claims, 9 Drawing Sheets

(56) References Cited

OTHER PUBLICATIONS

International Search Report for corresponding International Application No. PCT/KR2012/002084, mailed Nov. 5, 2012 (6 pages).

Written Opinion for corresponding International Application No. PCT/KR2012/002084, mailed Nov. 5, 2012 (9 pages).

* cited by examiner

Fig.8]

(a) Deep silicon etching  (b) PDMS molding
(c) PDMS punching
(d) PDMS spin coating  (e) PDMS bonding
(f) Detaching from substrate  (g) Cell injection Fig.12]
(a)
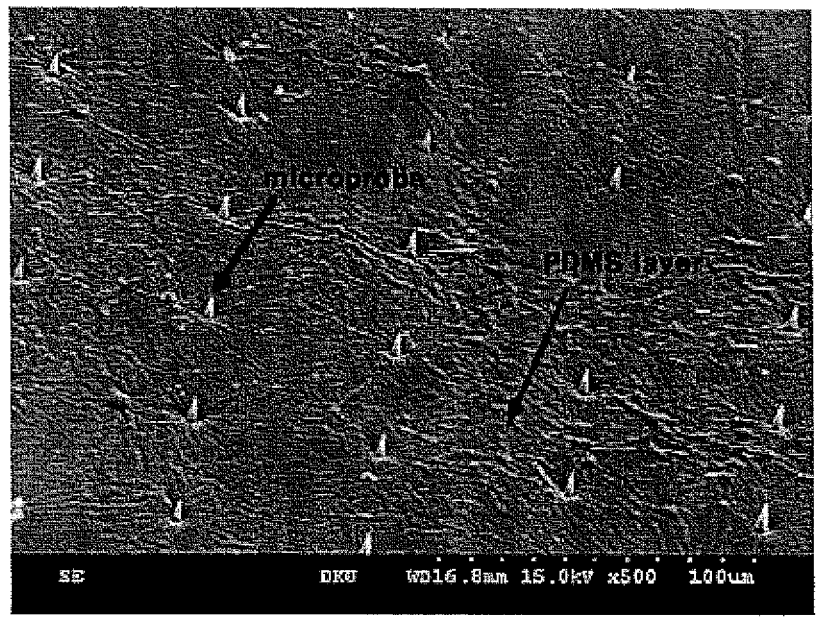
(b)
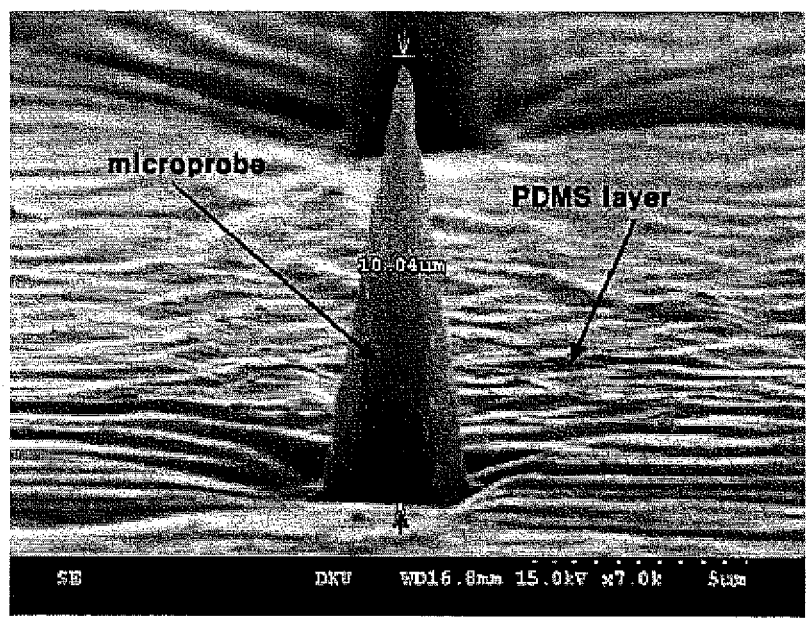

MICROBIAL FUEL CELL COMPRISING A MICROPROBE ARRAY

TECHNICAL FIELD

The present invention relates to a microbial fuel cell including a microprobe array, and more particularly, to a microbial fuel cell including a microprobe array, which has high energy efficiency, enables easy insertion of the microprobe to a plurality of cells, and facilitates replacement of used cells.

BACKGROUND ART

A microbial fuel cell (MFC) produces electricity using metabolic energy of bacteria, and all organic materials including waste may be fed by bacteria and thereby used to power of a fuel cell. The MFC that has been attracting attention as an alternative energy technology is a high efficiency energy conversion device which may use energy of pollutants in wastewater as fuel while removing the pollutants as food of microorganism, and directly recover electricity from the pollutants. Thus, when the MFC is used in wastewater treatment, clean energy may be provided, and effective treatment of wastewater may be possible.

FIG. 1 shows a basic operation process of a conventional MFC. Many elements are needed in order to produce an MFC, but three systems are basically needed. First, an anode for extracting electrons generated in a cell is needed. Second, a cathode for reducing the extracted electrons is needed. Third, an ion exchange membrane for separating the above-described two electrodes is needed. An existing MFC is operated in such a manner that the anode and the cathode are separated using an artificially produced thin film, electrons are extracted from a grouped cell in the anode, and oxygen supplied from the outside is reduced by the electrons in the cathode.

In many research institutions, research has been recently conducted into commercialization of the MFC. However, the biggest obstacle to the commercialization may be low energy density due to low efficiency.

DISCLOSURE

Technical Problem

The above-described low efficiency of the MFC is because a method of extracting electrons produced during a cell metabolic process in the anode positioned outside the grouped cell is used. In this case, it is difficult to extract electrons having high energy from an inside of the cell. That is, it is difficult to extract high efficiency energy using an external electrode from the grouped cell. In case of a general MFC, low energy density of about 0.1 to 1 $W/m^2$ has been presented. Thus, the recent research trend focuses on an increase in energy efficiency using carbon nanotubes (CNT) or changing a shape of an electrode. In recently presented research, energy density of about 1.5 $W/m^2$ by changing the shape of the electrode has been presented, but this may not be sufficient for actual application. Thus, energy density for commercialization cannot be achieved through existing research, and therefore there is a demand for developing a new type of the MFC.

Technical Solution

One aspect of the present invention provides a microbial fuel cell (MFC) including: a microfluidic element having an inlet portion and an outlet portion for intake and discharge of a culture fluid containing cells and a microchannel portion for capturing the cells and interconnecting the inlet portion and the outlet portion; a microprobe-array element having microprobes as anodes for extracting electrons produced during a metabolic process of the cells, and delivering the extracted electrons to an external circuit outside the cells; and a cathode for delivering the electrons used in the external circuit to an electron acceptor outside the cells, wherein the microprobes penetrate the microfluidic element and are inserted into a plurality of single cells captured by the microchannel portion when the microfluidic element and the microprobe-array element are coupled together, and the microprobes are separated from the single cells when the microfluidic element and the microprobe-array element are separated from each other.

Another aspect of the present invention provides an MFC including: a microprobe-array element having microprobes as anodes for being inserted into cells, extracting electrons produced during a metabolic process of the cells, and delivering the extracted electrons to an external circuit outside the cells; and a cathode for delivering the electrons used in the external circuit to an electron acceptor outside the cells, wherein the anode and the cathode are separated from each other by interposing a cell membrane of the cell.

Still another aspect of the present invention provides a microfluidic element for an MFC, including: an inlet portion for intake of a culture fluid containing cells; an outlet portion for discharge of the culture fluid; a microchannel portion for capturing the cells and interconnecting the inlet portion and the outlet portion; and a lower film for being penetrated by an external microprobe inserted into the cells within the microchannel portion and at the same time sealing so as to prevent leakage of the culture fluid within the microchannel portion after being penetrated.

DESCRIPTION OF DRAWINGS

FIG. 12 illustrates photos of SEM showing a state in which an actually manufactured microprobe array penetrates a PDMS thin film.

MODES OF THE INVENTION

Figure 1:
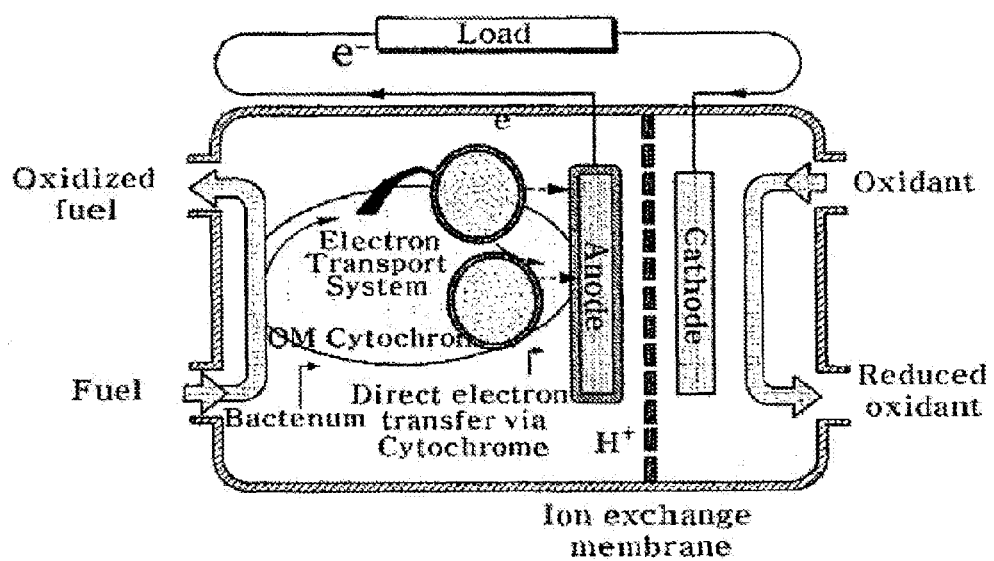
FIG. 1 illustrates a basic operation process of a conventional microbial fuel cell (MFC).

Hereinafter, embodiments of the present invention will be described in detail with reference to the accompanying drawings. However, the present invention is not limited to the exemplary embodiments disclosed below, but can be implemented in various forms. The following exemplary embodiments are described in order to enable those of ordinary skill in the art to embody and practice the invention. In the drawings, a width, a length, a thickness, and the like of a component may be exaggerated and expressed for convenience. Like numbers refer to like elements throughout the description of the figures. The figures are described from a point of view of an observer as a whole, and when a portion such as a layer, a film, or the like is "on" another portion, this includes a case in which still another portion is between the portion and the other portion as well as a case in which the portion is "directly on" the other portion.

Figure 2:
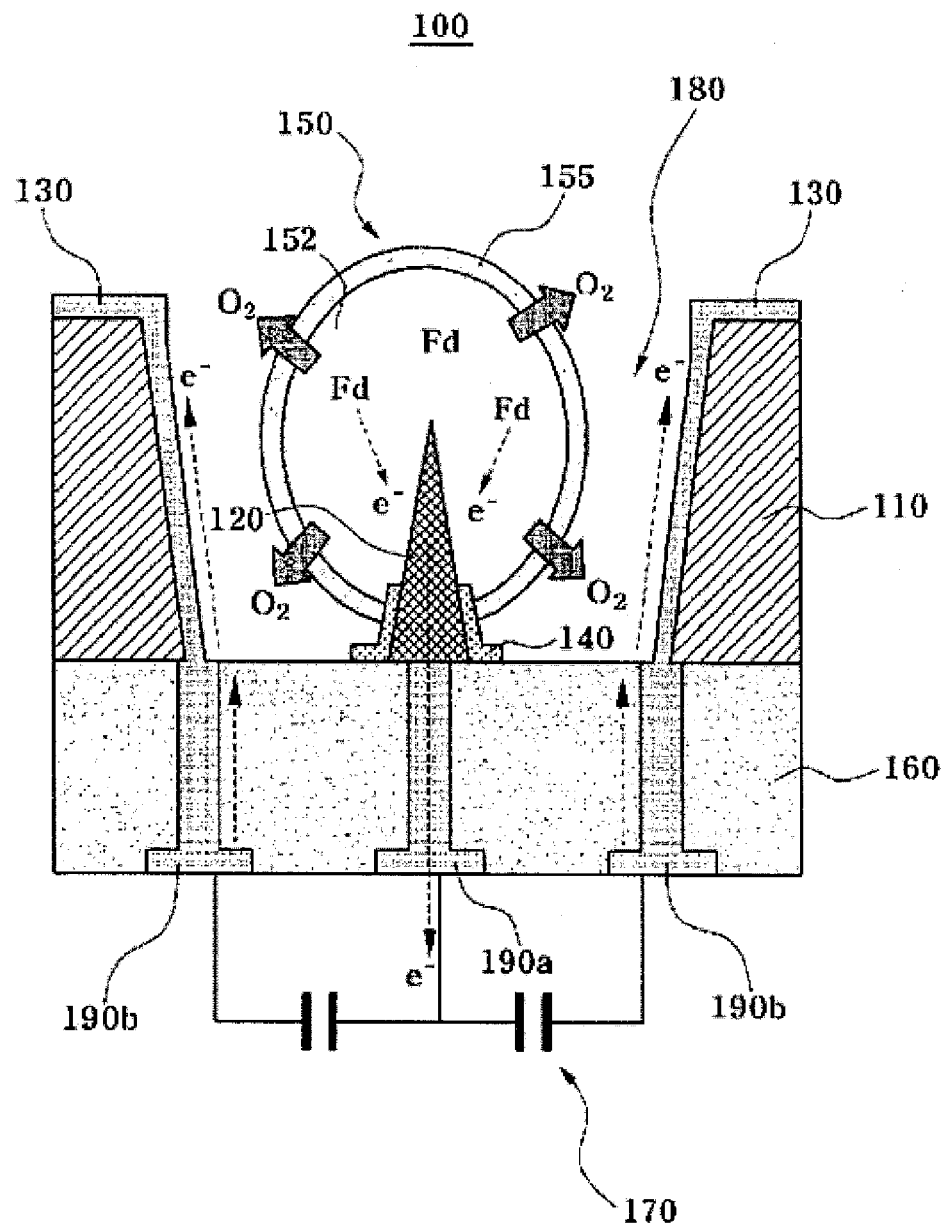
FIG. 2 is a schematic cross-sectional view illustrating an embodiment of an MFC according to the present invention.

FIG. 2 is a schematic cross-sectional view illustrating an embodiment of a microbial fuel cell (MFC) according to the present invention. Referring to FIG. 2, the MFC 100 according to the present invention includes a capturing portion 110 for capturing a single cell 150, a microprobe-shaped anode 120, and a cathode 130 as main components.

The capturing portion 110 has a size suitable for capturing a unit form, that is, the single cell 150 rather than a gathering of microbial cells. For example, the capturing portion 110 may have a well structure in which an outside of an inlet of the capturing portion 110 is large so that the single cell 150 is easily captured. A size of the single cell 150 used in the MFC 100 is about 5 to 20 μm, and therefore it is preferable that a size of the well structure be manufactured in the similar manner in accordance with types of the single cell 150. The well structure may be formed on a substrate 160 by semiconductor process technology. The substrate 160 includes a silicon or glass substrate, and includes various types in which application of the semiconductor process technology is possible.

The MFC 100 may operate as a fuel cell only after capturing the single cell 150 in the capturing portion 110. In this instance, the microbial cells are captured in units of single cells 150, and therefore the MFC 100 may become a single cell-based fuel cell that can use individual cells unlike the conventional MFC using a grouped cell. In order to capture the single cell 150 in the capturing portion 110, a microfluidic system or a dielectrophoresis (DEP) method may be used. The MFC 100 controls each of the single cells 150 to extract energy, thereby preventing energy from being wasted without being sufficiently used in the grouped cell.

The anode 120 is positioned on the same substrate 160 as the cathode 130, and at the same time, positioned within the capturing portion. The anode 120 includes a microprobe structure, and therefore may be inserted into the single cell 150 captured in the capturing portion 110. There is not a particular limitation on the single cell 150 as long as the single cell 150 is a microbe that can emit electrons by a metabolic process within the cell. The metabolic process may be photosynthesis. The anode 120 delivers the electrons produced during the metabolic process of the single cell 150 to an external circuit 170 outside the single cell 150.

The single cell 150 includes algae or photosynthesis microbes capable of undergoing photosynthesis by receiving external light such as sunlight, and other microbes capable of undergoing metabolism while producing electrons. The single cell 150 may cause an active metabolic process within the cell while growing in a culture fluid 180. When the single cell 150 undergoes metabolism that produces electrons such as photosynthesis, electrons are produced inside the cells to convert light energy into chemical energy while being subjected to various energy states. The electrons being in such various energy states may be converted into high efficiency energy as the electrons are extracted when having higher energy.

The anode 120 having the microprobe structure has a size of a micro- or nano-scale, and therefore penetrates a cell membrane 155 of the single cell 150 to be inserted therein. When a radius of curvature of a tip distal end in the microprobe structure is several tens of nm and a height to width ratio thereof is 5 or larger, the anode 120 may be easily inserted into the single cells 150. The microprobe structure may extract electrons being in the highest energy state among various stages of a photosynthesis metabolic process. Thus, for efficient energy conversion when extracting electrons of high energy, a material having a low charge transfer resistance of an electrode is preferably used as a material of the probe. For example, the microprobe structure may have carbon nanotubes (CNT) or nanowires, and a material such as platinum, gold, or graphite may be used. For example, as the microprobe structure, a glassy carbon electrode or a silicon probe coated with an ITO electrode may be used.

In case of the single cell 150 undergoing the photosynthesis metabolic process, when an electrode material is optimized, electrons being in the highest energy state among several stages of the photosynthesis metabolic process may be extracted. For example, electrons being in the high energy state coming from ferredoxin (Fd) by light energy in a first photosystem may be delivered directly from a filling liquid 152 within the single cells 150 to the anode 120 having the microprobe structure.

A process in which the microprobe structure penetrates the cell membrane 155 of the single cell 150 and is inserted therein may be performed in a pressure method or a suction method. For pressure, a pressure portion (not shown) may be provided above the MFC 100. When the pressure portion applies pressure on the single cell 150 against the culture fluid 180 in a direction of the anode 120, the microprobe structure may be inserted into the single cell 150, thereby extracting electrons within the cell. Meanwhile, when the process is performed in the suction method, a micro channel (not shown) such as a micro pipette is formed in the anode 120 having the microprobe structure, and a suction device (not shown) for intake of air or fluid positioned on a lower portion of the substrate 160 is provided to inhale the single cells 150 through the micro channel, and therefore the anode 120 having the microprobe structure may be inserted into the single cell 150. The microprobe structure even in any other forms may be implemented as long as an insertion process of the microprobe structure is a method using a pressure difference.

The microprobe structure may further include an insulation film 140. The insulation film 140 may protect a portion exposed when the anode is inserted into the single cell 150 so as to prevent the leakage of the extracted electrons from the filling liquid 152 within the single cell 150 to the cathode 130 when the extracted electrons are delivered to the external circuit 170.

The MFC 100 may further include connection electrodes 190a and 190b for connecting the anode 120 and the cathode 130 to the external circuit 170. In order to capture electrons to the outside from the single cells 150 which the MFC 100 captures, electrical connection is needed. In order to reduce an effect of external noise and reduce a loss due to a leakage current, a shorter length of an electrical connection portion connected from a unit fuel cell to the external circuit 170 is beneficial. Thus, for electrical connection, it is preferable that the connection electrodes 190a and 190b which penetrate the substrate 160 to be connected directly to the external circuit 170 are provided below the capturing portion 110.

The cathode 130 is a place in which a reduction reaction by the electrons used in the external circuit 170 occurs. The reduction reaction is a process of delivering the electrons used in the external circuit 170 to an electron acceptor outside the single cell 150. A type of the electron acceptor is not particularly limited, but may be oxygen that is produced in the metabolic process to be emitted to outside of the single cell 150. In the metabolic process of the single cell 150, the oxygen may penetrate the cell membrane 155 to be emitted to outside of the single cell 150, and the emitted oxygen may be reduced by the electrons in the cathode 130. For effective reduction reaction, the cathode 130 may be disposed in an inner wall of the capturing portion 110.

The anode 120 and the cathode 130 are separated from each other through the cell membrane 155 of the single cell 150. Therefore, the MFC according to the present invention may use the cell membrane as an ion exchange membrane, and use the oxygen produced in the cell in the reduction reaction of the electrode, and therefore the MFC may be a self-sustained MFC.

In the MFC 100 according to the present invention, electrode reactions which respectively occur in the anode 120 and the cathode 130 may be processed as follows:

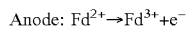

Anode: $Fd^{2+} \rightarrow Fd^{3+} + e^-$    i)

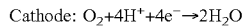

Cathode: $O_2 + 4H^+ + 4e^- \rightarrow 2H_2O$    ii)

As a material for entering the cell membrane, oxygen and H⁺ and other various ions for matching pH may be moved.

Figure 3:
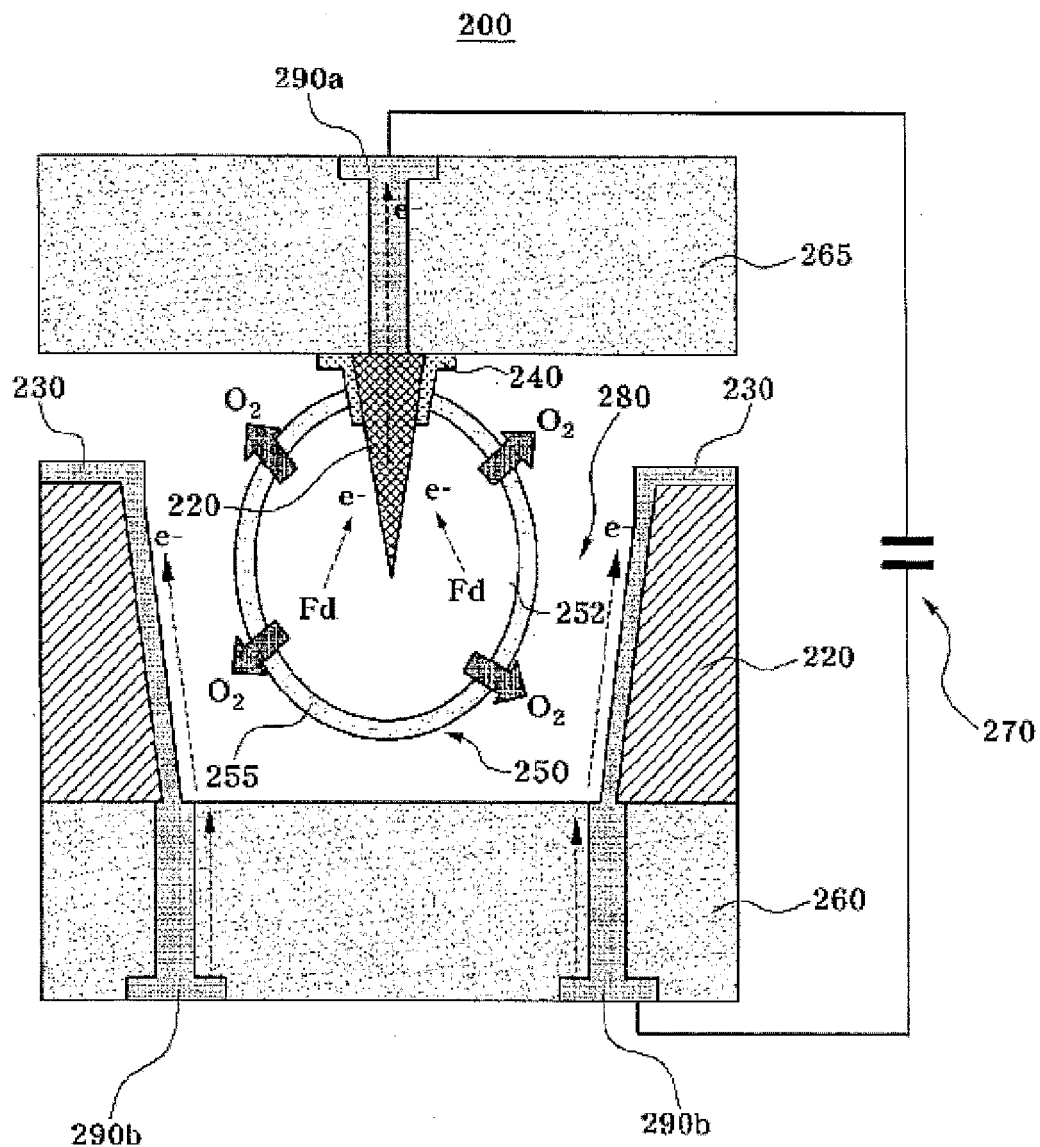
FIG. 3 is a schematic cross-sectional view illustrating another embodiment of an MFC according to the present invention.

FIG. 3 is a schematic cross-sectional view illustrating another embodiment of an MFC according to the present invention.

Referring to FIG. 3, like FIG. 2, an MFC 200 according to an embodiment of the present invention includes a capturing portion 210 for capturing single cells 250, a microprobe-shaped anode 220, and a cathode 230 as main components.

A difference between the present embodiment and the embodiment of FIG. 2 is that the anode 220 is not positioned in the capturing portion 210 of a first substrate 260 but positioned in a second substrate 265 facing the first substrate 260. That is, the anode 220 is positioned on the separate substrate facing the cathode 230, and at the same time, positioned outside the capturing portion 210.

The anode 220 and the cathode 230 are positioned on separate substrates, and therefore a micro process with respect to each substrate when manufacturing the MFC 200 may be relatively easy. In addition, the single cell 250 is captured within the capturing portion 210, and then the microprobe structure of the anode 220 presses the single cell 250 by directly controlling a distance between the first substrate 260 and the second substrate 265, and therefore the anode 220 may be inserted into the single cell 250. In this case, a separate pressure portion may not be needed.

Detailed descriptions of other components 210, 220, 230, 240, 250, 252, 255, 260, 270, 280, 290a, and 290b which are described or not described in the present embodiment are the same as the components 110, 120, 130, 140, 150, 152, 155, 160, 170, 180, 190a, and 190b, and thus repeated descriptions will be omitted.

The MFC described in the above-described embodiments are excellent at its energy efficiency and density compared to the conventional MFC, but an absolute energy amount in a level of a unit fuel cell may not be sufficient. Thus, according to an embodiment of the present invention, there is provided an MFC array having a two-dimensional (2D) array structure in which an MFC is included as unit fuel cells and a plurality of unit fuel cells are electrically connected to each other, or having a three-dimensional (3D) array structure in which the 2D array structures are stacked. In case of the 3D array structure, electrical connection of the 2D array structures may be achieved through a connection structure penetrating substrates. In this manner, by implementing the MFC in the form of array having a multi-array structure, extracted energy amount may be increased.

Figure 4:
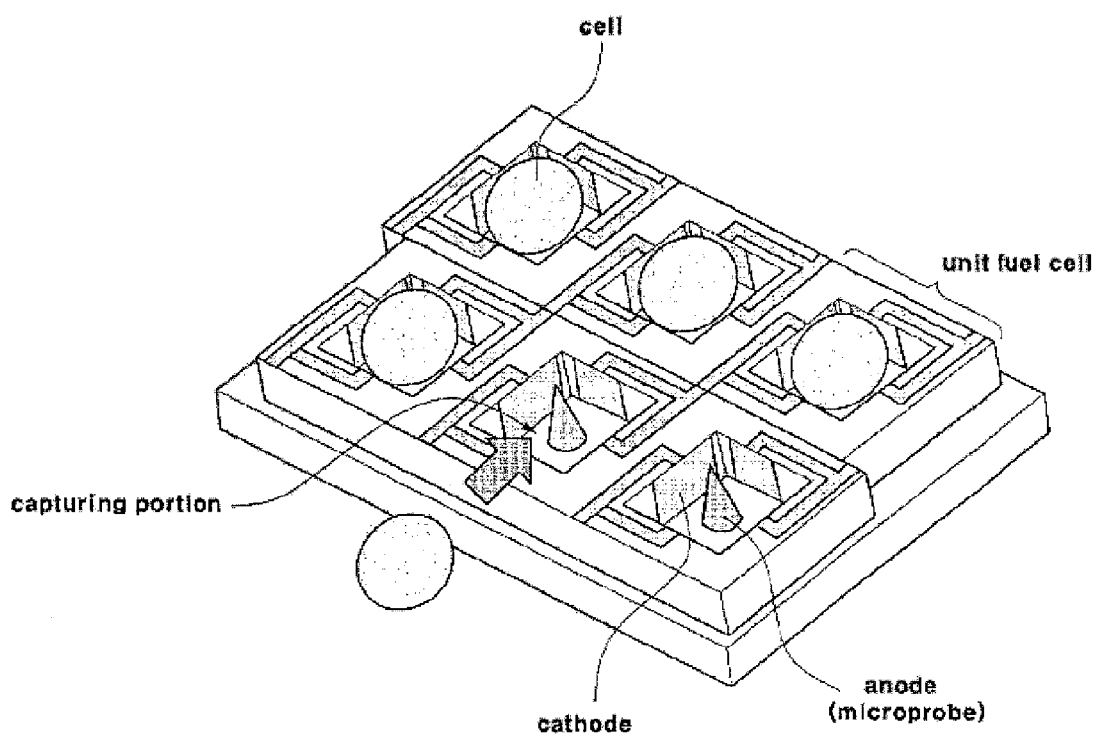
FIG. 4 is a schematic perspective view illustrating an MFC array having a multi-array structure according to an embodiment of the present invention.

FIG. 4 is a schematic perspective view illustrating an MFC array having a multi-array structure according to an embodiment of the present invention. Referring to FIG. 4, the MFC structure in the form of unit fuel cells is formed in the form of array connected in a 2D manner, thereby extracting a large amount of energy. Using an electrode connection structure in each of the unit cells, electrons are extracted, and the extracted electrons are captured in an external circuit, thereby enabling utilization and storage of energy. The MFC array may be manufactured by micro process technology such as MEMS/NEMS.

Meanwhile, when using the MFC array structure, it is necessary that a plurality of cells are inserted into microprobes within unit fuel cells, respectively. In this instance, the insertion of the single cell into each of the microprobes is technically very difficult, and a large number of unit fuel cells are required to extract a sufficient amount of energy, and therefore the insertion of the cell into each of the microprobes may be a very inefficient method. In addition, when functions of the cells inserted into the microprobes are lost over time, a method for easily replacing the cells and inserting the replaced cells into the microprobes is required.

According to an embodiment of the present invention, there is provided a new MFC which easily inserts the microprobes into a large number of cells and easily replaces the cells to insert the microprobes into the replaced cells.

Figure 5:
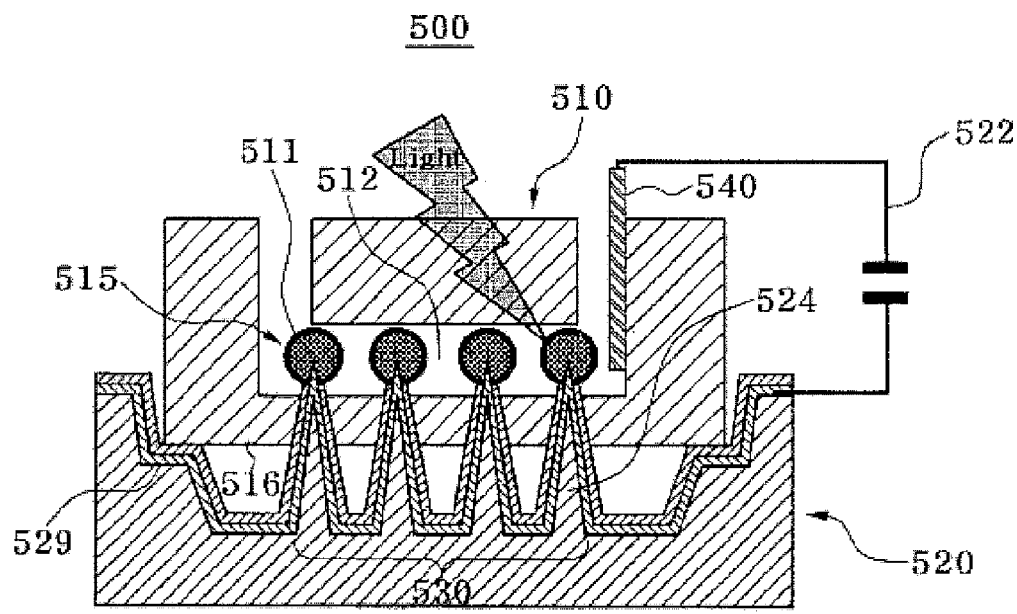
FIG. 5 is a schematic view illustrating an MFC having a microprobe array according to an embodiment of the present invention.

FIG. 5 is a schematic view illustrating an MFC having a microprobe array according to an embodiment of the present invention. In addition, FIG. 6 illustrates a microfluidic element for capturing cells and supplying a cell culture fluid, as a part of an MFC, and FIG. 7 illustrates a microprobe-array element including microprobes for extracting electrons from cells, as a part of an MFC.

Referring to FIG. 5, in an MFC 500, a microfluidic element 510 in which cells 511 are captured and a cell culture fluid 512 is supplied and a microprobe-array element 520 which is inserted into the cells 511 to extract high energy electrons produced during a metabolic process such as photosynthesis of the cells 511 to outside the cells 511 are coupled together. A cathode 540 delivers electrons used in an external circuit 522 to an electron acceptor outside the cells 511. The electron acceptor may be oxygen which is produced during the metabolic process and emitted to outside of the cells 511.

Figure 6:
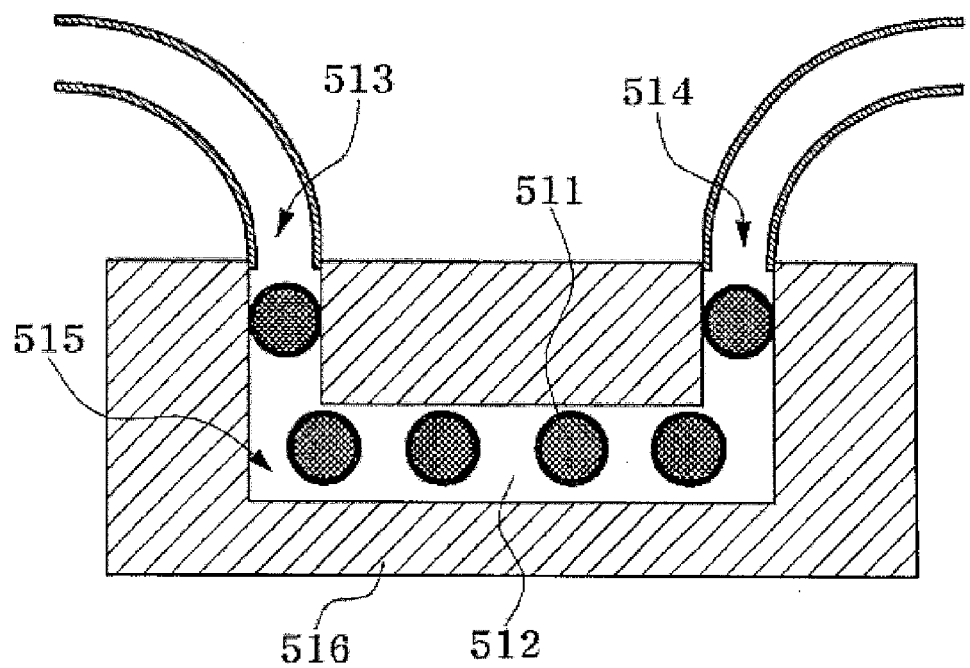
FIG. 6 illustrates a microfluidic element for capturing cells and supplying a cell culture fluid, as a part of an MFC.

Referring to FIG. 6, the microfluidic element 510 may include an inlet portion 513 and an outlet portion 514 for intake and discharge of the culture fluid 512 containing the cells 511 and a microchannel portion 515 for capturing the cells 511 and interconnecting the inlet portion 513 and the outlet portion 514.

Figure 7:
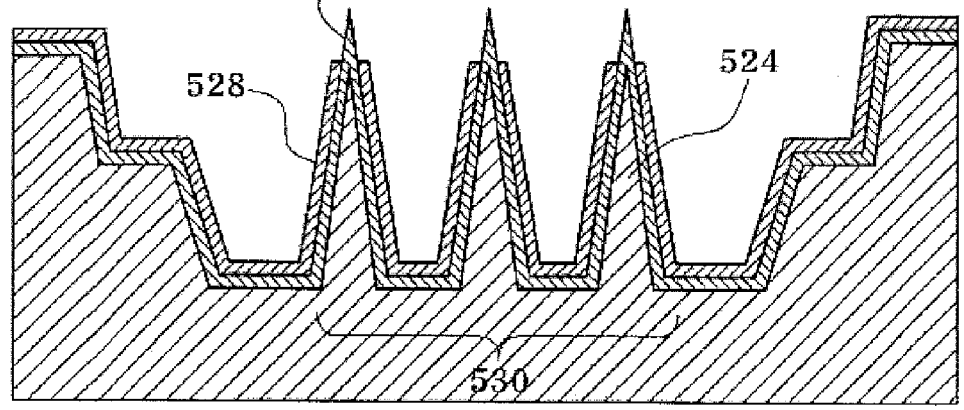
FIG. 7 illustrates a microprobe-array element including microprobes for extracting electrons from cells, as a part of an MFC.

Referring to FIG. 7, the microprobe-array element 520 includes microprobes 524 as anodes 530 for extracting the electrons produced during the metabolic process of the cells 511, and delivering the extracted electrons to the external circuit 522 outside the cells 511.

The anode 530 extracts electrons being in a high energy state within the cells 511. Thus, for efficient energy conversion when extracting the electrons of high energy, it is important to manufacture a material having a low charge transfer resistance of the electrodes as a material of the microprobe 524. The microprobe 524 may be a probe having a micro-or nano-meter scale. The microprobe 524 may be manufactured in the form of tip by processing a substrate such as silicon, coated with an electrode material capable of extracting electrons, and then a portion except a tip portion 526 which is inserted into the cells may be coated with an insulation film 528. The insulation film 528 may protect a portion exposed to the outside excluding the portion inserted into the cells 511 so as to prevent efficiency from being reduced due to the leakage of the extracted electrons from a cell filling liquid to the cathode 540 when the extracted electrons are delivered to the external circuit 522.

Referring to FIG. 5 again, the microfluidic element 510 may include a transparent or semi-transparent portion so that external light required for the metabolic process of the cells 511 can penetrate the microfluidic element 510. For example, a body of the microfluidic element 510 may be made of a silicone resin such as polydimethylsiloxane (PDMS) so that the external light required for photosynthesis can penetrates the microfluidic element 510. In addition, the microfluidic element 510 may include a lower film 516 made of a material which the microprobes 524 can penetrate when the microfluidic element 510 and the microprobe-array element 520 are coupled together. For example, the lower film 516 may be made of a very thin silicone resin.

When the microfluidic element 510 and the microprobe-array element 520 are coupled together, the microprobes 524 may be inserted into a large number of cells 511 captured in the microchannel portion 515 while penetrating the microfluidic element 510. When the microfluidic element 510 and the microprobe-array element 520 are coupled together, the anode 530 and the cathode 540 may be separated from each other by interposing a cell membrane of the cells 511.

Meanwhile, when the microfluidic element 510 is separated from the microprobe-array element 520, the microprobes 524 may be separated from the cells 511. The separated microfluidic element 510 may be replaced with a new microfluidic element, and the replaced microfluidic element may be coupled with the microprobe-array element 520.

When using the above-described MFC, the large number of single cells may be easily inserted into the microprobes, and only the microfluidic element may be replaced after use and coupled, thereby easily replacing the cells.

The microprobe-array element 520 may further include a step portion 529 so that a coupling height is adjusted when the microfluidic element 510 and the microprobe-array element 520 are coupled together, other than the microprobes 524. Since the microfluidic element 510 is latched to the step portion 529 when being coupled with the microprobe-array element 520, the microprobes 524 may penetrate up to an appropriate position in which the microprobes 524 are inserted into the cells 511. In addition, by adjusting a thickness of the lower film 516 of the microfluidic element 510, a height in which the microprobes 524 penetrate and are inserted into the cells 511 may be adjusted. Through such a method, an appropriate structure capable of being utilized in various kinds of cells having various sizes may be easily implemented.

Figure 8:
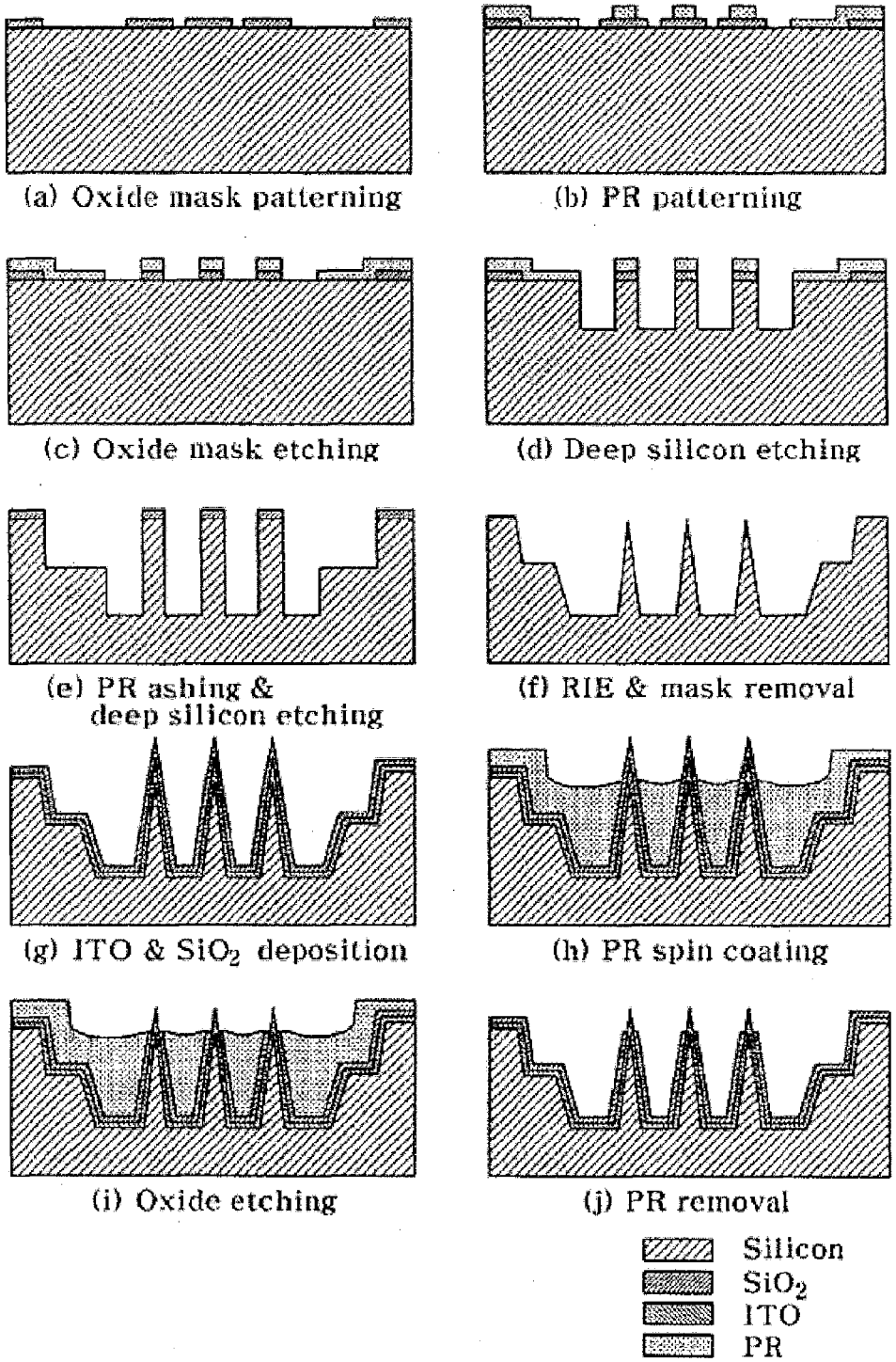
FIG. 8 illustrates a method for manufacturing a microprobe array according to an embodiment of the present invention.

The microprobe-array element 520 may be manufactured in a method in which a manufacturing process is simple, a high yield is obtained, and low costs are realized. FIG. 8 illustrates a method for manufacturing a microprobe array according to an embodiment of the present invention. Referring to FIG. 8, for silicon etching realizing two steps, each of a silicon oxide film ($SiO_2$) etching mask and a photoresist film is patterned to form two layers (see, FIGS. 8A to 8C).

Silicon is vertically etched by a predetermined depth in a deep reactive ion etching (DRIE) process using the photoresist film as an etching mask (see, FIG. 8D). In this instance, an etching depth may be a height from a bottom of the microprobe to a step for connection adjustment in a final structure.

After the photoresist film is removed, the silicon is vertically etched again using the oxide film as a mask (see, FIG. 8E). Until this process, a vertical silicon column rather than a probe having a tip is made.

When the silicon is isotropically etched below the etching mask through a reactive ion etching (RIE) process, the microprobe having a pointed top is manufactured (see, FIG. 8F).

Next, a high conductive electrode material (ITO) favorable to extract high energy electrons within the cells is coated on the silicon probe, and an insulation film ($SiO_2$) is formed for insulation of the remaining portions except a tip portion inserted into the cells (see, FIG. 8G).

In order to etch the insulation film deposited up to a distal end of the probe for being inserted into the cells, a photoresist film is coated in a method such as spin coating. In this instance, the tip of the probe is coated with the photoresist film to have a relatively thinner thickness due to the step of the probe (see, FIG. 8H).

Thus, when performing an oxide film etching process by a silicon oxide film etching equipment in this state, the photoresist film having a thin thickness at the distal end of the probe is first etched, and then an exposed oxide film is etched (see, FIG. 8I).

Finally, like FIG. 8J, a microprobe array in which the electrode is exposed only in the tip portion of the probe and the remaining portions are surrounded by the insulation film may be manufactured.

Figure 9:
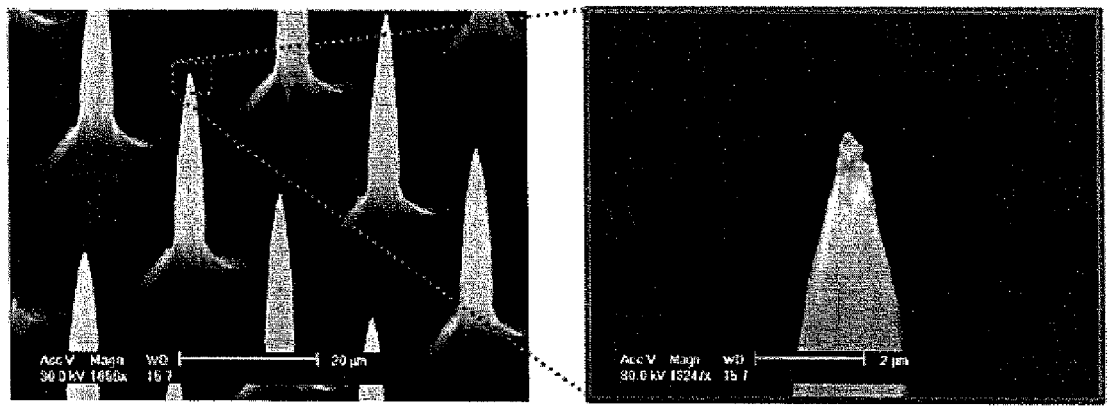
FIG. 9 illustrates photos of a scanning electron microscope (SEM) of an actually manufactured microprobe array.

FIG. 9 illustrates photos of a scanning electron microscope (SEM) of an actually manufactured microprobe array. In the right photo of FIG. 9, an electrode is exposed in a tip portion of a microprobe.

Other than the above-described manufacturing method, by utilizing the conventional various metal probe manufacturing methods or a focused ion beam (FIB) etching method, the microprobe array may be manufactured.

Figure 10:
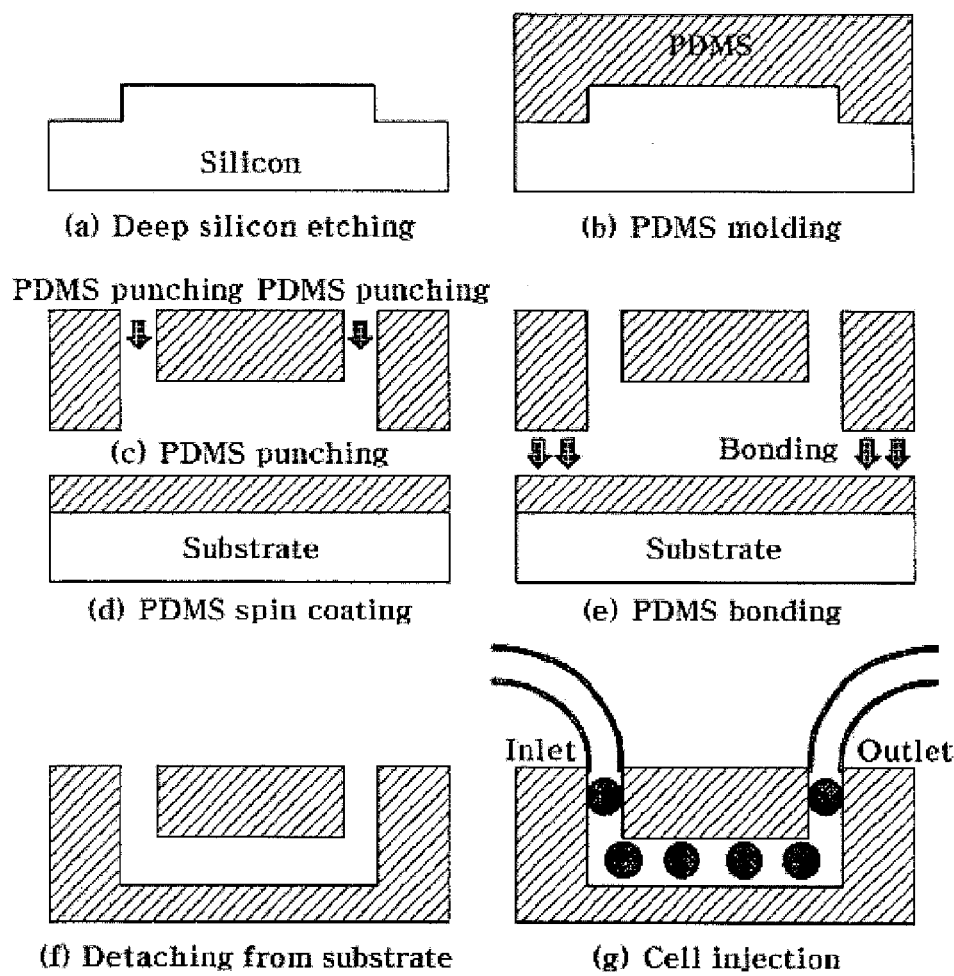
FIG. 10 illustrates a method for manufacturing a microfluidic element according to an embodiment of the present invention.

FIG. 10 illustrates a method for manufacturing a microfluidic element according to an embodiment of the present invention.

The microfluidic element is preferably manufactured using a transparent material so that cells captured in the microfluidic element can undergo photosynthesis. In addition, a lower film of the microfluidic element is preferably manufactured using a material which can be penetrated by a microprobe and does not cause leakage of the fluid or cracks after the penetration. For this, polydimethylsiloxane (PDMS) is spin-coated on the substrate to form a thin film, and the thin film is bonded to a lower portion of the microfluidic element made of PDMS, and therefore the lower film which the microprobe penetrates may be manufactured.

Referring to FIG. 10, in order to manufacture a shape of the microfluidic element, silicon is vertically etched using a DRIE process (see, FIG. 10a). In this instance, an etching depth is adjusted so as to enable capturing within the channel to be easy considering the size of the cell.

When the PDMS is poured and hardened on the etched silicon pattern using the etched silicon pattern as a mold, a fluidic channel is formed (see, FIG. 10b).

The PDMS is separated from the silicon, and then the PDMS is drilled for creating an inlet in which cells and fluid are injected and an outlet (see, FIG. 10c).

In order to form the lower portion of the microfluidic element as the thin PDMS film which the microprobe can penetrate, the PDMS is spin-coated on a silicon or glass substrate (see, FIG. 10d). By adjusting a rotation speed when performing spin-coating, the PDMS thin film with a desired thickness may be manufactured.

When the coated PDMS surface and the PDMS surface in which the channel pattern is formed are bonded with each other, the microfluidic element is completed (see, FIGS. 10e and 10f).

In FIG. 10g, a conceptual diagram in which a tube is connected to the manufactured microfluidic element and then cells are injected and captured is shown. After the cells are captured in this manner, and then the microfluidic element is aligned with the microprobe-array element and coupled together, thereby completing a final structure.

Figure 11:
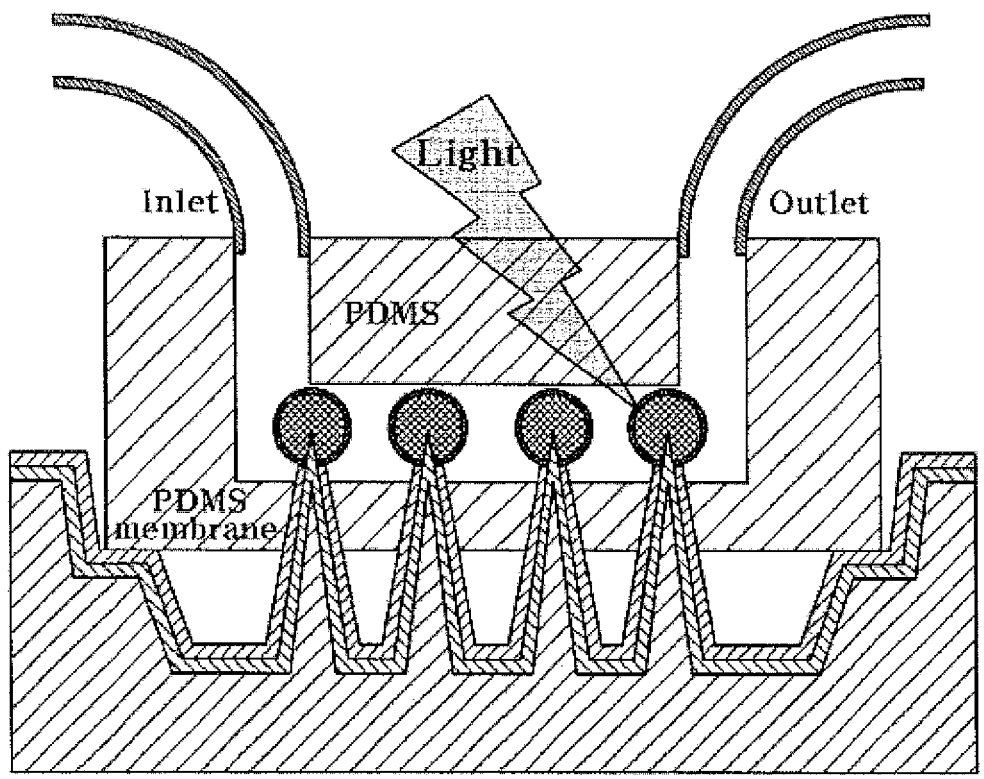
FIG. 11 is a cross-sectional view illustrating a final structure in which a microfluidic element and a microprobe-array element are coupled together.

FIG. 11 is a cross-sectional view illustrating a final structure in which a microfluidic element and a microprobe-array element are coupled together. Referring to FIG. 11, when external light penetrates a transparent PDMS body and arrives at the cells within the microfluidic channel, the cells may undergo photosynthesis, and in this process, the high energy electrons are extracted to the outside by the microprobe. When using the MFC according to the present invention, a cell culture liquid may be continuously supplied to the cells in a process of extracting energy, and new cells may be inserted into the microprobe by simply replacing the microfluidic element.

FIG. 12 illustrates photos of SEM showing a state in which an actually manufactured microprobe array penetrates a PDMS thin film. From FIG. 12, it can be seen that the microprobe penetrates the PDMS thin film and the PDMS thin film has no cracks.

In the MFC according to the present invention, unlike the conventional MFC, electrons of high energy may be extracted by inserting the electrode into each of single cells rather than a grouped cell, thereby obtaining high efficiency. In addition, energy wasted without being sufficiently used in the grouped cell may be extracted, thereby obtaining higher efficiency.

In addition, the cell membrane within the cells may be used instead of an ion exchange membrane without using a separate ion exchange membrane. The conventional MFC additionally requires an ion exchange membrane for separating electrodes and a separate device for continuously supplying oxygen from the outside for a reduction reaction. This is a big obstacle to system miniaturization and affects system performance due to reliability and a lifespan of a thin film, and therefore there arises a problem in commercialization. On the other hand, the MFC according to the present invention may use oxygen produced within the cells in the reduction reaction of the electrodes, and therefore an additional thin film is not required to be manufactured, and continuous oxygen supply from the outside is not required. As a result, the MFC according to the present invention may be a self-sustained MFC having a simple system. As a result, the size of the system can be dramatically reduced, thereby significantly increasing energy density.

In addition, since the anode may be positioned within the cells, there is no need to use a redox medium for electron extraction which may cause a toxic problem. In the MFC according to the present invention, unit fuel cells having high efficiency are accumulated in a 2D or 3D manner to be expanded as an array, and thus output may be further maximized.

In addition, in the MFC having a structure in which the microfluidic channel element and the microprobe-array element are coupled together, when functions of the cells inserted into the microprobe are lost over time, the cells may be easily replaced and the replaced cells may be inserted into the microprobe.

When using the MFC according to the present invention, eco-friendly clean energy may be produced with high efficiency and implemented as a very compact device, and therefore the conventional electrochemical cell or solar cell may be replaced with the MFC according to the present invention. In addition, in an energy production process, carbon dioxide may be removed by utilizing microbial cells and oxygen may be produced, and therefore the MFC according to the present invention may be utilized as environmental clean-up technologies. Other MFC technologies based on single cells according to the present invention may be applied to technology for utilizing and measuring the photosynthesis and metabolic process of cells to contribute to the development of environmental sensor manufacturing technologies.

While the invention has been shown and described with reference to certain exemplary embodiments thereof, it will be understood by those skilled in the art that various changes in foil and details may be made therein without departing from the spirit and scope of the invention as defined by the appended claims.

The invention claimed is:

1. A microbial fuel cell (MFC) comprising:
    a microfluidic element having an inlet portion and an outlet portion for intake and discharge of a culture fluid containing cells and a microchannel portion for capturing the cells and interconnecting the inlet portion and the outlet portion;
    a microprobe-array element having microprobes as anodes for extracting electrons produced during a metabolic process of the cells, and delivering the extracted electrons to an external circuit outside the cells; and
    a cathode for delivering the electrons used in the external circuit to an electron acceptor outside the cells,
    wherein the microprobes penetrate the microfluidic element and are inserted into a plurality of single cells captured by the microchannel portion when the microfluidic element and the microprobe-array element are coupled together, and the microprobes are separated from the single cells when the microfluidic element and the microprobe-array element are separated from each other.

2. The MFC of claim 1, wherein the microfluidic element includes a transparent or semi-transparent portion which external light required for the metabolism of the cells penetrates.

3. The MFC of claim 1, wherein the microfluidic element includes a lower film made of a material which the microprobes penetrate when the microfluidic element and the microprobe-array element are coupled together.

4. The MFC of claim 3, wherein the material is a silicone resin.

5. The MFC of claim 1, wherein the microprobe further includes an insulation film for protecting a portion exposed when the microprobes are inserted into the cells so as to prevent leakage of the extracted electrons from filling liquid within the cell to the cathode when the extracted electrons are delivered to the external circuit.

6. The MFC of claim 1, wherein the microprobe-array element further includes a step portion so that a coupling height is adjusted when the microprobe-array element and the microfluidic element are coupled together.

7. The MFC of claim 1, wherein the electron acceptor is oxygen that is produced during the metabolic process to be released to the outside of the cell.

8. The MFC of claim 1, wherein the anode and the cathode are separated from each other by interposing a cell membrane of the cell when the microfluidic element and the microprobe-array element are coupled together.

* * * * *